United States Patent

Rosenblatt et al.

[11] Patent Number: 5,807,581
[45] Date of Patent: Sep. 15, 1998

[54] COLLAGEN-BASED INJECTABLE DRUG DELIVERY SYSTEM AND ITS USE

[75] Inventors: Joel S. Rosenblatt, Palo Alto; Richard A. Berg, Los Altos, both of Calif.

[73] Assignee: Collagen Corporation, Palo Alto, Calif.

[21] Appl. No.: 537,073

[22] Filed: Sep. 29, 1995

Related U.S. Application Data

[63] Continuation of Ser. No. 193,600, Feb. 9, 1994, abandoned.

[51] Int. Cl.$^6$ .................................................. A61K 9/08
[52] U.S. Cl. .................. 424/484; 424/422; 424/424; 424/426; 424/485; 424/486; 424/487; 604/890.1
[58] Field of Search ................. 424/489, 450, 424/422, 424, 426, 484, 485, 486, 487; 514/21, 54; 604/890.1

[56] References Cited

U.S. PATENT DOCUMENTS

| | | | |
|---|---|---|---|
| 3,949,073 | 4/1976 | Daniels et al. | 424/177 |
| 4,164,559 | 8/1979 | Miyata et al. | 424/14 |
| 4,165,599 | 8/1979 | Lenorak | 57/58.83 |
| 4,179,337 | 12/1979 | Davis et al. | 435/181 |
| 4,358,442 | 11/1982 | Peitz | 424/199 |
| 4,424,208 | 1/1984 | Wallace et al. | 424/177 |
| 4,488,911 | 12/1984 | Luck et al. | 106/161 |
| 4,557,764 | 12/1985 | Chu | 106/161 |
| 4,582,640 | 4/1986 | Smestad et al. | 260/123.7 |
| 4,642,117 | 2/1987 | Nguyen et al. | 623/11 |
| 4,689,399 | 8/1987 | Chu | 530/356 |
| 4,703,108 | 10/1987 | Silver et al. | 530/356 |
| 4,820,857 | 4/1989 | Palmer et al. | 558/277 |
| 4,861,714 | 8/1989 | Dean, Jr. et al. | 435/68 |
| 4,863,856 | 9/1989 | Dean, Jr. et al. | 435/68 |
| 4,925,924 | 5/1990 | Silver et al. | 530/356 |
| 4,938,763 | 7/1990 | Dunn | 604/891.1 |
| 4,970,298 | 11/1990 | Silver | 530/356 |
| 4,997,753 | 3/1991 | Dean, Jr. et al. | 435/69.1 |
| 5,162,430 | 11/1992 | Rhee et al. | 525/54.1 |
| 5,198,465 | 3/1993 | Dioguardi | 514/474 |
| 5,318,780 | 6/1994 | Viegas | 424/427 |

FOREIGN PATENT DOCUMENTS

| | | | |
|---|---|---|---|
| 0160266 | 11/1985 | European Pat. Off. | A61K 9/50 |
| 0509338A1 | 10/1992 | European Pat. Off. | A61K 9/127 |
| 3912693A1 | 10/1990 | Germany | A61L 15/42 |
| 4028622A1 | 3/1992 | Germany | C08H 1/06 |
| 85/04413 | 10/1985 | WIPO | A61K 9/22 |
| WO92/14445 | 9/1992 | WIPO | A61K 9/127 |
| WO92/14447 | 9/1992 | WIPO | A61K 9/127 |
| 94/01483 | 1/1994 | WIPO | A61K 9/00 |

OTHER PUBLICATIONS

J. Rosenblatt et al., "Chain Rigidity and Diffusional Release in Biopolymer Gels", *Proceed. Intern. Symp. Control. Rel. Bioact. Mater.*, vol. 20, pp. 264–265 (1993).

E. Kakizaki, *Derwent Publications Ltd., Dabase WPI*, AN88–116590 and JP/63063624, Week 8817, Mar. 22 (1988).

Abuchowski et al., *Enzymes as Drugs*, Ch. 13, pp. 367–383, John Wiley & Sons: New York, NY (1981).

Dreborg et al., "Immunotherapy with Monomethoxpolyethylene Glycol Modified Allergens", *Crit. Rev. Therap. Carrier Syst.*, vol. 6, Iss. 4, pp. 315–365, (1990).

(List continued on next page.)

*Primary Examiner*—Gollamudi S. Kishore
*Attorney, Agent, or Firm*—Morrison & Foerster, LLP

[57] ABSTRACT

Drugs are delivered in a sustained manner from an in vivo depot which is formed from a collagen-based injectable composition. The injectable composition is fluid when injected but undergoes crosslinking in situ to form a crosslinked collagen matrix which encloses the drug to be released. The composition also includes a flexible chain polymer which is similarly charged to the precrosslinked collagen. This flexible chain polymer is enclosed in the matrix as well when the matrix forms and alters the effective porosity of the matrix. The drug diffuses out of the matrix at a rate which depends upon the matrix's effective porosity.

49 Claims, 2 Drawing Sheets

OTHER PUBLICATIONS

Mutter et al., "The Liquid–Phase Method for Peptide Synthesis", *The Peptides,* vol. 2, Ch. 2, pp. 286–332, Academic: New York, NY (1979).

Zalipsky et al., "A Convenient General Method forSynthesis on $N^\beta$ or $N^\omega$–Dithiasuccinoyl (Dts) Amino Acids and Dipeptides: Application of Polyethylene Glycol as A Carrier for Functional Purification", *Int. J. Peptide Protein Res.,* 30, 740–783 (1987).

Zalipsky et al., "Attachment of Drugs to Polyethylene Glycols", *Eur. Polym J.,* vol. 19, No. 12, pp. 1177–1183 (1983).

Ouchi et al., "Sytheses of 5–Fluorouracil–Terminated Monomethoxypoly(Ethylene Glycols)s. Their Hydrolysis Behavior, and their Anitumor Activities", *J. Macromol. Sci. Chem.,* A24 (9), pp. 1011–1032 (1987).

Nucci et al., "The Therapeutic Value of Poly(Ethytene Glycol)–Modified Proteins", *Advanced Drug Delivery Reviews,* 6, pp. 133–151 (1991).

Weiner et al., "Liposome–Collagen Gel Matrix: A Novel Sustained Drug Delivery System", *J. Pharm Sci.,* vol. 74, No. 9, pp. 922–925 (1985).

Johansson et al., "Diffusion and Interaction in Gels and Solutions", *Macromolecules,* vol. 24, No. 22, pp. 6019–6023 (1991).

Phillies, "The Hydrodynamic Scaling Model for Polymer Self–Diffusion", *J. Phys. Chem,* vol. 93, No. 13, pp. 5029–5039 (1989).

Doi et al., *The Theory of Polymer Dynamics,* Ch. 9, pp. 324–349, Clarendon Press, Oxford (1986).

Rosenblatt et al., "The Effect of Collagen Fiber Size Distribution on The Release Rate of Proteins from Collagen Matrices by Diffusion", *J. Controlled Release,* 9, pp. 195–203 (1989).

De Smedt et al., "Structural Information on Hyaluronic Acid Solutions As Studied by Probe Diffusion Experiments", *Macromolecules,* vol. 27, No. 1, pp. 141–146 (1994).

COLLAGEN-BASED INJECTABLE DRUG DELIVERY SYSTEM AND ITS USE

This application is a continuation application of prior U.S. application Ser. No. 08/193,600, filed Feb. 9, 1994, now abn.

TECHNICAL FIELD

This invention concerns a system for sustaining the delivery of drug to a patient. More particularly, it concerns a collagen-based injectable drug delivery system and its use to achieve delivery of drug to a patient at a sustained rate over a prolonged time period.

BACKGROUND OF THE INVENTION

Over the past 25 years there has been an ever-increasing understanding that the way in which drugs are administered to patients can play a large role in their efficacy. A variety of systems for controlling and sustaining the delivery of drugs to patients have been proposed. These have included systems in which the rate of drug delivery is controlled by the rate at which the drug is osmotically pumped from a reservoir, the rate at which the drug is cleaved from a support, the rate at which the drug is released by an enclosing covering and the rate at which the drug diffuses through a membrane or out of a matrix, to name but a few common modalities.

These systems for drug delivery can be used in a variety of manners. For example, they can be placed on drug permeable body membranes, such as on the skin or the mucosa of the mouth, in body cavities such as the stomach, lower bowel or conjunctiva of the eye, or can be used in vivo by injection or implantation. The present invention concerns a system which is fluid at the time of administration and thus lends itself to injection.

The drug delivery systems of this invention employ collagen as a component. Collagen has been mentioned as a component of drug delivery systems but not, to our knowledge, in the context of the present systems of this invention.

Collagen is the major protein component of bone, cartilage, skin, and connective tissue in animals. Collagen in its native form is typically a rigid, rod-shaped molecule approximately 300 nm long and 1.5 nm in diameter. It is composed of three collagen polypeptides which form a tight triple helix. The collagen polypeptides are characterized by a long midsection having the repeating sequence -Gly-X-Y-, where X and Y are often proline or hydroxyproline, bounded at each end by the "telopeptide" regions, which constitute less than about 5% of the molecule. The telopeptide regions of the collagen chains are typically responsible for the cross-linking between chains, and for the immunogenicity of the protein. Collagen occurs in several "types", having differing physical properties. The most abundant types are types I–III.

Collagen is typically isolated from natural sources, such as bovine hide, cartilage, or bones. Bones are usually dried, defatted, crushed, and demineralized to extract collagen, while hide and cartilage are usually minced and digested with proteolytic enzymes (other than collagenase). As collagen is resistant to most proteolytic enzymes, this procedure conveniently serves to remove most of the contaminating protein found with collagen.

Daniels et al, U.S. Pat. No. 3,949,073, disclosed the preparation of soluble collagen by dissolving tissue in aqueous acid, followed by enzymatic digestion. The resulting atelopeptide collagen is soluble, and substantially less immunogenic than unmodified collagen. This material is now commercially available from Collagen Corporation (Palo Alto, CA) under the tradename Zyderm® Collagen Implant.

Luck et al, U.S. Pat. No. 4,488,911, disclosed a method for preparing collagen in solution (CIS), wherein native collagen is extracted from animal tissue in dilute aqueous acid, followed by digestion with an enzyme such as pepsin, trypsin, or Pronase®. The enzymatic digestion removes the telopeptide portions of the collagen molecules, providing "atelopeptide" collagen in solution. The atelopeptide CIS so produced is substantially non-immunogenic, and is also substantially non-crosslinked due to loss of the primary crosslinking regions. The CIS may then be precipitated by dialysis in a moderate shear environment to produce collagen fibers which resemble native collagen fibers. The precipitated, reconstituted fibers may additionally be crosslinked using a chemical agent (for example, aldehydes such as formaldehyde and glutaraldehyde), heat, or radiation.

Smestad et al, U.S. Pat. No. 4,582,640, disclosed a glutaraldehyde crosslinked atelopeptide CIS preparation (GAX) suitable for use in medical implants. The collagen is crosslinked under conditions favoring intrafiber bonding rather than inter-fiber bonding. Such product is commercially available from Collagen Corporation under the tradename Zyplast® Collagen Implant.

The following series of related patents disclosed various types of collagen containing materials. The patents are U.S. Pat. Nos. 4,703,108, issued Oct. 27, 1987; 4,861,714, issued Aug. 29, 1989; 4,863,856, issued Sep. 5, 1989; 4,925,924, issued May 15, 1990; 4,970,298, issued Nov. 13, 1990; and 4,997,753, issued Mar. 5, 1991. These patents disclosed collagen materials wherein type I, II, and III collagens were contacted with a crosslinking agent selected from the group consisting of a carbodiimide or a succinimydyl active ester.

Rhee et al., U.S. Pat. No. 5,162,430 described the use of hydrophilic synthetic polymers to chemically conjugate collagen. The possibility of incorporating biologically active factors, such as epidermal growth factor, with the conjugate was disclosed as was the possibility of causing the reaction between the collagen and synthetic polymer to be carried out in situ following injection. This patent mentioned that the hydrophilic crosslinking polymer can bind collagen to glycosaminoglycans, chondroitin sulfates, fibronectin and growth factors and that the tethering can provide an effective slow-release drug delivery system.

As further background, it should be pointed out that coinventor Rosenblatt and others studied the rate release of drugs from mixtures of noncrosslinked collagen and flexible polymers at the University of Maryland prior to the filing of this application.

DISCLOSURE OF THE INVENTION

It has now been discovered that drugs can be delivered in a sustained manner from an in vivo depot which is formed from a collagen-based injectable composition. In preferred embodiments, the injectable composition is fluid when injected but undergoes crosslinking in situ to form a crosslinked collagen matrix which encloses the drug to be released. The composition also includes a flexible chain polymer which is electrostatically or ionically similar in charge to the precrosslinked collagen. This flexible chain polymer is enclosed in the matrix as well and alters the effective porosity of the matrix. The drug diffuses out of the matrix at a rate which depends upon the matrix's effective porosity and rigidity.

Thus, in one embodiment this invention provides an injectable sustained-release drug delivery formulation. This formulation includes collagen, a crosslinking agent capable of forming covalent bonds in situ following injection with the collagen, a flexible chain polymer similar in charge to the collagen, and a drug in a pharmaceutically acceptable injectable carrier.

In another embodiment, this invention provides a sustained-release subdermal drug delivery depot. This depot may be formed from the above-described injectable formulation. The depot includes a drug and a flexible chain polymer entrapped within a porous matrix of crosslinked collagen. The flexible chain polymer alters the effective pore size of the matrix of crosslinked collagen to a size which sustains the diffusion of the drug from the matrix into a subdermal environment.

In yet an additional embodiment, this invention provides a method for preparing a sustained-release subdermal drug delivery depot. This method includes forming a fluid admixture of the drug, collagen, flexible chain polymer and a collagen crosslinking agent in an injectable medium, injecting this fluid admixture into said patient under conditions which limit the immediate dispersion of the admixture and which permit the crosslinking agent to crosslink the collagen and form in situ a matrix from which the drug can diffuse to the patient.

In a further embodiment, this invention provides a method for delivering drug to a patient in a sustained and controlled manner over an extended period of time. This drug delivery method involves forming a fluid admixture of the drug, collagen, flexible chain polymer and a collagen crosslinking agent in an injectable medium, injecting this fluid admixture into said patient under conditions which limit the immediate dispersion of the admixture and which permit the crosslinking agent to crosslink the collagen and form a matrix and then permitting this matrix to remain in place in the patient over an extended period of time during which the drug can diffuse from the matrix to the patient.

In a yet further embodiment, this invention provides another method for delivering drug to a patient in a sustained and controlled manner over an extended period of time. This drug delivery method involves delivering the drug to the patient by diffusion from an in vivo depot, the depot comprising the drug entrapped in a porous matrix of crosslinked collagen, the matrix additionally enclosing a flexible chain polymer and the flexible chain polymer altering the rate at which the drug can diffuse from the matrix to the patient.

BRIEF DESCRIPTION OF THE DRAWINGS

This invention will be further described with reference being made to the drawings in which.

DETAILED DESCRIPTION OF PREFERRED EMBODIMENTS OF THE INVENTION

Figure 1:
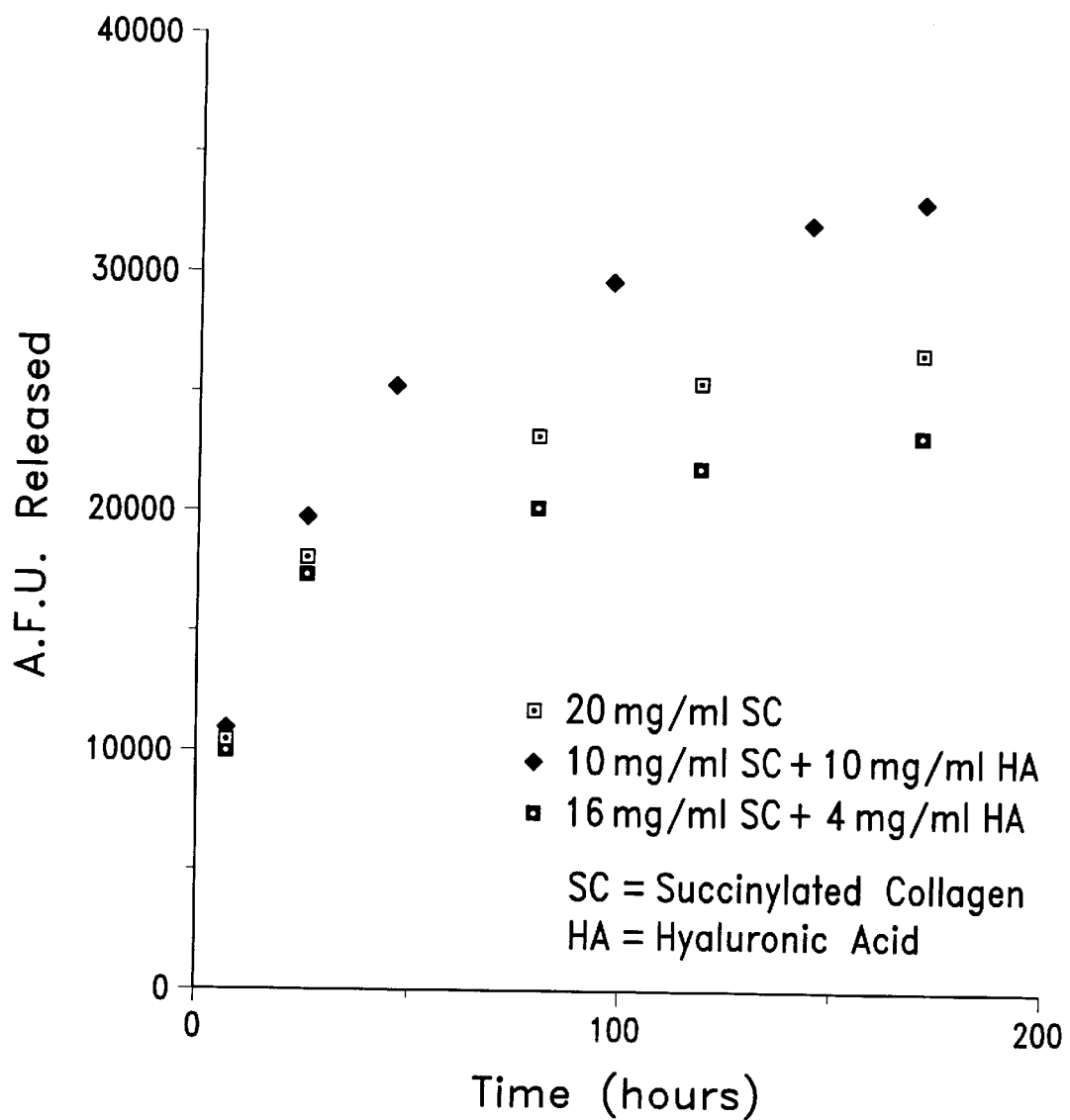
FIG. 1 is a graph illustrating the rate of release of drug from collagen-based matrices containing no added flexible polymer and varying amounts of flexible polymer.

This Detailed Description is broken down into the following subsections based upon the materials employed in this invention:

Collagen
Crosslinking Agents
Flexible Chain Polymers
Drugs
Overall Injectable Compositions
Depot Characteristics
Methods of Preparation
Methods of Use These subsections are followed by Examples setting out embodiments of the invention.

Collagen

The term "collagen" as used herein refers to all forms of collagen as are described above in the background section, including those which have been processed or modified. The collagen may be of human or animal origin and may be produced by recombinant techniques. The present invention can use these and other known types of collagen including natural collagen and various collagen derivatives.

Preferred collagens are non-immunoreactive, atelopeptide collagen, with types I, II, and III being preferred. Collagens may be soluble (for example, commercially available Vitrogen® 100 collagen-in-solution), and may or may not have the telopeptide regions. Collagen can be in the form of reconstituted fibrillar atelopeptide collagen, for example Zyderm® Collagen Implant (ZCI) but preferably is non-fibrillar atelopeptide collagen in solution (CIS) such as the Vitrogen material. Various forms of collagen are available commercially, or may be prepared by the processes described in, for example, U.S. Pat. Nos. 3,949,073; 4,488,911; 4,424,208; 4,582,640; 4,642,117; 4,557,764; and 4,689,399, all incorporated herein by reference. Mixtures of various types of collagen as well as fibrillar collagen, nonfibrillar collagen and mixtures thereof can be used. Nonfibrillar, atelopeptide collagen in solution is preferred.

If fibrillar collagen or other crosslinked collagen is used as a starting material, it may be of advantage to chop, shred or grind it into a suspendible particulate size so that suitable injectable materials may be prepared from it.

Collagen (and even previously crosslinked collagen) contains a number of available amino, carboxy and hydroxy groups which may be used as sites for crosslinking. These groups are capable of taking on various charges at different pH conditions. For example, the amine groups can take on a positive charge and become ammonium groups at pHs below amount 8. Similarly, carboxyl groups can be uncharged or negatively charges depending upon whether they are ionized or have lost their acidic hydrogen.

One aspect of this invention calls for the crosslinked collagen and the flexible chain polymer to be similarly charged so as to mix and be compatible. Thus, it is often desirable to adjust the charge of the collagen at neutral pH. Ways for doing this are well documented in the literature. For example, one can esterify the carboxyl groups to eliminate their ability to take on a negative charge at neutral pH and impart it to the collagen. Methylation of the carboxyl groups is the most common esterification but of course other similar nontoxic blocking groups can be employed if desired. The amino groups present in lysines in the collagen can be converted into amides by reaction with an active amide-forming agent. Examples of this step include succinylation and glutarylation of the available amines. Miyata et al. described methods which can be used to alter the net ionic charge of collagen in U.S. Pat. No. 4,165,559. This patent is incorporated by reference.

In addition to methods for altering the charge of collagen which are based upon blocking ionizable groups appearing in the native protein, one can also alter the collagen's charge by grafting species to the collagen which contain sulfonates, phosphonates, phosphates and/or various ionizable amines and the like so as to impart a desired charge to the collagen. Depending on the nature of the reactive molecule, a carboxyl group may be incorporated for each amine undergoing reaction.

Crosslinking Agents

The preferred materials of this invention additionally include one or more crosslinking agents. Suitable crosslinkers should be nontoxic when administered by injection as part of the injectable mixtures of this invention. They also should not be subject to rapid dispersal into the patient's body when injected.

In theory, one could employ any of the crosslinking agents known in the art for crosslinking collagen. These include simple aldehyde crosslinkers such as formaldehyde and glutaraldehyde, carbodiimides and the succinimydyl active-esters. Preferably, however, polymer-based crosslinkers are employed. These materials are preferred because of their larger molecular size which is reflected in lower toxicity and a lower rate of dispersal upon injection. These polymeric crosslinking agents are typically based upon hydrophilic polymers, both naturally occurring and synthetic.

The term "synthetic hydrophilic polymer" as used herein refers to a synthetic polymer having an average molecular weight and composition which renders the polymer substantially water-compatible. Preferred polymers are highly pure or are purified to a highly pure state such that the polymer is or is treated to become pharmaceutically pure. Most hydrophilic polymers can be rendered hydrophilic and even water-soluble by incorporating a sufficient number of oxygen (or less frequently nitrogen) atoms available for forming hydrogen bonds in aqueous solutions. Preferred polymers are hydrophilic and preferably (but not necessarily) water-soluble. Hydrophilic polymers used herein include poly-(ethylene glycol) (PEG), poly(oxyethylene), poly-(methylene glycol), poly(trimethylene glycol), poly (vinylpyrrolidone), and derivatives thereof with PEG being particularly preferred. The polymers can be linear or multiply branched, and will not be substantially crosslinked. Other suitable polymers include poly(oxyethylene)-poly (oxypropylene) block polymers and copolymers. Poly (oxyethylene)-poly(oxypropylene) block polymers having an ethylene diamine nucleus (and thus having four ends) are also available and may be used in the practice of the invention.

Naturally occurring polymers such as proteins, starch, cellulose, dextran, and the like while not falling within the definition of "synthetic" hydrophilic polymers, do qualify as "hydrophilic" polymers and are not excluded from use in the practice of this invention. Because of the ease of obtaining pure materials, the synthetic polymers are preferred.

All suitable polymers will be non-toxic, non-inflammatory, and non-immunogenic when administered subcutaneously, and will preferably be essentially nondegradable in vivo over a period of at least several hours and preferably at least several (i.e. two) days.

Since these polymers serve as crosslinking agents for the collagen, they should contain at least two sites capable of reacting with and binding to collagen. Although not a limitation to the scope of this invention, it should be noted that the collagen molecules contain hydroxyl groups and free amino groups in the form of lysine residues. The hydroxyl groups can react to form ether and ester linkages and the free amino groups can form covalent amide bonds in cross-linking reactions with acid or active ester groups present in the polymeric crosslinkers. These acid or ester groups can be incorporated into the polymeric crosslinkers through ether links which are in turn formed from hydroxyl groups, and particularly activated hydroxyl groups on the hydrophilic polymers although other equivalent sites may be employed.

Collagen contains a number of available amino and hydroxy groups which may be used as sites to form crosslinks. The collagen may be coupled to the crosslinker using a "linking group", as the native hydroxy or amino groups in collagen and in the polymer frequently require activation before they can be linked. For example, one may employ compounds such as dicarboxylic anhydrides (e.g., glutaric or succinic anhydride) to form a polymer derivative (e.g., succinate), which may then be activated by esterification with a convenient leaving group, for example, N-hydroxysuccinimide, N,N'- disuccinimidyl oxalate, N,N'-disuccinimidyl carbonate, and the like. See also Davis, U.S. Pat. No. 4,179,337 (incorporated by reference) for additional linking groups. Various functionalized polyethylene glycols have been used effectively in fields such as protein modification (see Abuchowski et al., *Enzymes as Drugs,* John Wiley & Sons: New York, N.Y. (1981) pp. 367–383; and Dreborg et al., *Crit. Rev. Theran. Drug Carrier Syst.* (1990) 6:315, both of which are incorporated herein by reference), peptide chemistry (see Mutter et al., *The Peptides,* Academic: New York, N.Y. 2:285–332; and Zalipsky et al., *Int. J. Peptide Protein Res.* (1987) 30:740, both of which are incorporated herein by reference), and the synthesis of polymeric drugs (see Zalipsky et al., *Eur. Polym. J.* (1983) 19:1177; and Ouchi et al., *J. Macromol. Sci.—Chem.* (1987) A24:1011, both of which are incorporated herein by reference).

Presently preferred dicarboxylic anhydrides that are used to form activated crosslinking polymers include glutaric anhydride, adipic anhydride, 1,8-naphthalene dicarboxylic anhydride, and 1,4,5,8-naphthalenetetracarboxylic dianhydride. The polymer thus activated is then allowed to react with the collagen, forming a collagen-polymer crosslinked composition.

Presently preferred hydrophilic polymer crosslinkers are di- and multifunctional polyethylene glycols (PEG). Difunctional PEG may have its two reactive sites at any position along its chain but typically has a reactive hydroxy group at each end, while a polyfunctional material will have additional groups along its chain.

Difunctional PEG preferably has an average molecular weight of about 400 Da to about 100 kDa, more preferably about 3 kDa to about 10 kDa. Multifunctional PEG preferably has an average molecular weight between about 3 kDa and 100 kDa. Similar sizes are preferred for other equivalent crosslinkers, as well.

Those of skill in the art will appreciate that synthetic polymers such as poly(ethylene glycol) cannot be prepared practically to have exact molecular weights, and that the term "molecular weight" as used herein refers to the average molecular weight of a number of molecules in any given sample, as commonly used in the art. Thus, a sample of PEG 3,000 might contain a statistical mixture of polymer molecules ranging in weight from, for example, 1.5 to 4.5 kDa with one molecule differing slightly from the next over a range. Specification of a range of molecular weight indicates that the average molecular weight may be any value between the limits specified, and may include molecules outside those limits. Thus, a molecular weight range of about 3 kDa to about 10 kDa indicates an average molecular weight of at least about 3 kDa and ranging up to about 10 kDa.

Flexible Chain Polymers

The compositions of this invention include one or more flexible chain polymers. The flexible chain polymers which are present in the compositions of this invention should be biocompatible, non-toxic, non-inflammatory, and non-immunogenic when administered subcutaneously, and will preferably be essentially nondegradable in vivo over the same period as the crosslinking material (several hours and preferably several days).

The flexible chain polymers should have the same sign charge as the charge on the collagen prior to crosslinking. Both materials can be positively charged, both can be negatively charged or both can be uncharged. Most commonly both materials will be charged. The charge identity allows the two materials to mix intimately without precipitation as might occur between polymers of different charge. Hydrophilic flexible chain polymers are preferred because of their ability to mix with collagen and to pick up water when present in the matrix.

The flexible chain polymer is characterized by its relative persistence length. It should have a persistence length not greater than 0.1 times the persistence length of the collagen with which it is mixed. Collagen typically has a persistence length on the order of 150 nm or 250 nm. Flexible chain polymers should have persistence lengths of less than 15 nm and especially less than 10 nm and more especially from 2 to 5 nm. Another characteristic of the flexible chain polymers is that they have a molecular weight on the order of 100 kDa or greater and especially greater than about 500 kDa and more especially greater than about 1000 kDa.

The flexible chain polymer can be a synthetic material. Representative synthetic materials include, for example:

poly(acrylic acid)
poly(vinyl alcohol)
poly(acrylamide)
poly(N-isopropylacrylamide)
poly(methacrylate)
poly(hydroxyethylmethacrylate)
poly(vinyl acetate)
copolymers and derivatives of these materials and the like.

The flexible chain polymer can be a naturally occurring material or a derivative of a naturally occurring material such as a glycosaminoglycan, a cellulose, or a poly(nucleic acid).

The glycosaminoglycans are complex polysaccharides having repeating units of either the same saccharide subunit or different saccharide subunits. Some examples of glycosaminoglycans include hyaluronic acid, the chondroitin sulfates, chitin, chitosan and derivatives of all or any of these materials. In general, the glycosaminoglycans are extracted from a natural source, purified and derivatized. However, they may be synthetically produced by microorganisms such as bacteria.

Hyaluronic acid encompasses naturally occurring and synthetic forms of the polymer having the formula

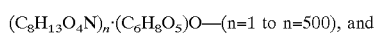

$(C_8H_{13}O_4N)_n \cdot (C_6H_8O_5)O$—(n=1 to n=500), and derivatives thereof. The compound includes alternating units of 1,4-linked N-acetylglucosamine and glucuronic acid units as shown below.

HYALURONIC ACID

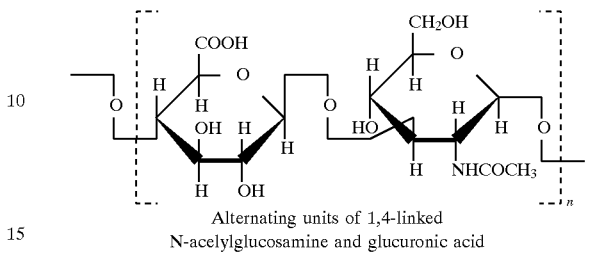

Alternating units of 1,4-linked
N-acetylglucosamine and glucuronic acid

Hyaluronic acid is a viscous, high molecular weight mucopolysaccharide found in mammalian fluids and connective tissue. Hyaluronic acid typically is obtained with a molecular weight greater than about 1000 kDa and often greater than about 2000 kDa.

There are three major compounds encompassed by the term "chondroitin sulfate". These are chondroitin sulfate A, dermatan sulfate (also known as chondroitin sulfate B, an isomer of chondroitin sulfate A) and chondroitin sulfate C. The structures of these three compounds are shown below.

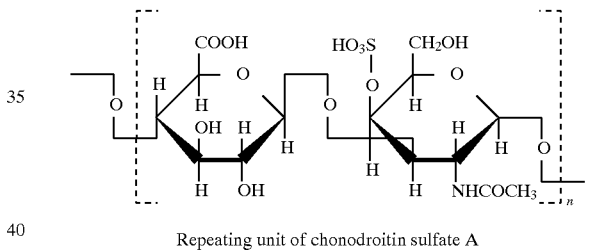

Repeating unit of chonodroitin sulfate A

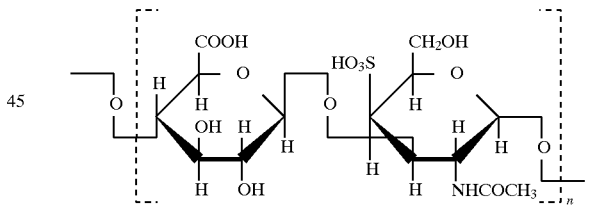

Repeating unit of chonodroitin sulfate C

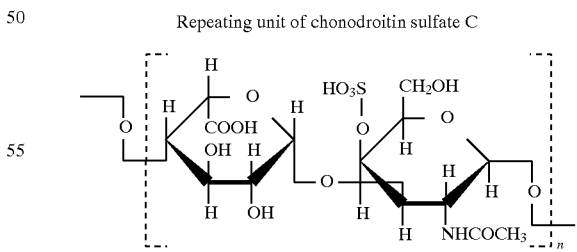

Repeating unit of dermatan sulfate
(chonodroitin sulfate B)

Chitin encompasses polymers comprising repeating units of N-acetylglucosamine. The structure of chitin is shown below.

CHITIN

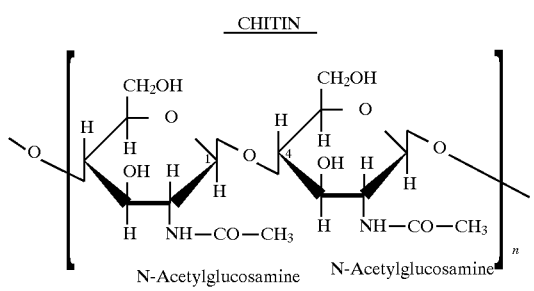

The term "chitosan" covers both partially and fully deacetylated chitin, as shown below.

CHITOSAN

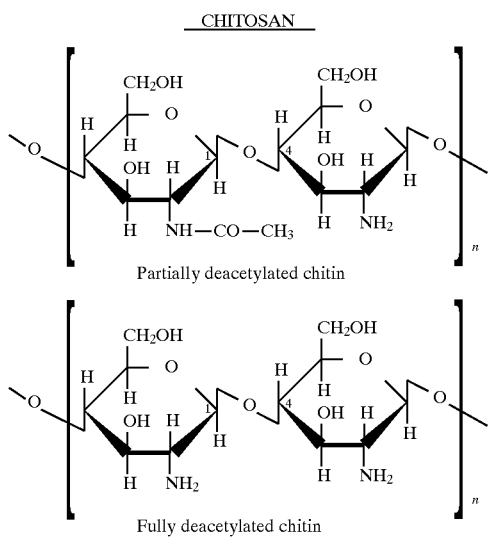

Partially deacetylated chitin

Fully deacetylated chitin

Drugs

The drugs which are delivered by the systems of this invention are typically present in a macromolecular form. The term "drug, as used herein is defined to encompass not only compounds or species which are themselves inherently pharmacologically or biologically active but also materials which include one or more of these active compounds or species combined with, bonded to, or otherwise associated with other materials such as polymers, carriers, encapsulants and the like.

The systems of this invention operate on principles of diffusion from a porous matrix. On a molecular scale the matrix consists of a set of intersecting threads which create a mesh-work as opposed to cylindrical tunnels or holes in a solid substrate. The matrix pore sizes are on the order of 3 to 30 nanometers in average diameter. The pore sizes can be made larger by using a set of larger interconnecting threads to create a more open meshwork. Fibrillar collagen-based matrices typically have larger matrices with pore sizes of up to 100 nM or greater. For pore sizes of 3 nanometers, there is minimal diffusion rate control with small or low molecular weight drugs having a molecular weight of a few hundred daltons, say.

Drugs having a molecular weight (or apparent molecular weight) of at least about 10 kDa and as high as 1000 kDa or higher may be used with matrices having a pore size of 3 to 30 nanometers. From a size point of view such materials have a size which will substantially interact with and be substantially restricted by the cross-linked rigid matrix. This occurs with drugs having a size of, for example at least about 3 nM along their largest axis. Preferred drugs are 4–5 nM or larger along their longest axis.

These drugs can be molecules which themselves have these desired high weights and large sizes. Such materials include clotting factors, growth factors and cytokines to name but three representative classes. Clotting factors include Factor 8, Factor 9 and protein C. Cytokines include macrophage colony stimulating factor (MCSF) and erythropoetin.

Some of these potential drugs are materials such as proteins which in theory could react with the cross-linking agent and be themselves bound into the crosslinked collagen network. This would not be desirable as this bonding would likely prevent the drug's release, as desired. This undesired effect can be avoided by protecting or blocking potentially reactive sites on the drug. Poly(ethylene glycol) can be reacted with the drug to prevent these undesirable reactions. This step, referred to as "PEGylating" the drug can be carried out on the drug prior to mixing the drug with matrix and in situ crosslinking. This will prevent the drug from being tethered to the matrix, thus ensuring that it can be released from the matrix. PEGylation techniques and their positive effect on drugs are described in Nucci et al., Advanced Drug Delivery Reviews (1991) 6:133-51, which is incorporated by reference.

In addition to these representative inherently large drugs, one can also administer smaller drugs if they have been associated with or bound to a carrier molecule so as to give a suitably great apparent molecular weight. This can be accomplished by covalently bonding the drug to the carrier in a manner which permits the drug to retain its biological activity or in a manner which allows the drug to be cleaved off of the backbone following its release rate controlling diffusion from the crosslinked collagen/flexible polymer matrix.

The active species can also be tethered to a polymer or like carrier by ionic bonds or by immunologic (antibody/antigen) binding, using biotin/avidin binding, or by hydrophobic or hydrogen bonding. Similarly, multiple units of a small species may be coupled together or grafted onto a polymer backbone to achieve the desired large size drug.

Carriers for coupling to active pharmaceuticals to increase their size can be of natural or synthetic origin. Representative materials include the glycosaminoglycans, as previously described, flexible polymers, proteins, carbohydrates and the like. Examples include starch, dextran, fibronectin, albumin, particularly human albumin, synthetic polymers such as poly(vinyl amine), monofunctional PEG and the like.

In addition, a small active species may be physically engulfed into a liposome or other similar physical structure to give a drug particle of a size suitable for sustained release from the present systems (Weiner et al., J. Pharm. Sci. (1985) 74 (9):922-5; Dougardi, U.S. Pat. No. 5,198,465; European Patent Application 509338 (1992); European Patent Application 525132 (1993); European Patent Application 525167 (1993); German Patent Application 4028622 (1992); German Patent Application 3912693 (1990); and Handjani et al., U.S. Pat. No. 4,820,857, all incorporated by reference for disclosing various liposome compositions and their preparation). Liposomes and the like are often relatively quite large, i.e., several tens of nanometers or even much larger. Such materials often work best with matrices based on fibrillar collagen which can provide pore sizes which will accommodate species of this size.

Active species may be linked to PEG to increase their molecular weight (Nucci et al. supra) and provide the desired large drugs. Such species may be glycosylated using polysaccharides, again to increase their molecular weight. A small active entity can also be encapsulated into emulsified fat and the like. With all of these possibilities, all of which are well documented in the literature, the system of the present invention can be made to operate and gradually release virtually any drug. The term drug is used in its broadest sense, also, to include vitamins, nutrients, promoters, as well as pharmaceutical substances. Examples of suitable drugs include without limitation the above described factors, anti-inflammatories, hormones, antibiotics, and the like.

The drug delivery system of this invention is especially useful for large, glycosylated drugs. The sustained delivery of Factor 8 is another desirable therapy which could be accomplished using this system.

Overall Compositions

The injectable compositions provided by this invention are mixtures of materials. The proportions of the various materials are as follows:

| | |
|---|---|
| Collagen | 0.1 to 10% by weight of the overall injectable composition |
| Crosslinker | 0.1 to 5% by weight of the overall injectable composition |
| Flexible | 0.1 to 15% by weight of the overall injectable polymer composition |
| Drug | 0.001 to 10% by weight of the overall injectable composition |

These materials are dispersed (dissolved or suspended) in a suitable injectable carrier, creating an injectable matrix. This carrier can range from injectable saline to any other pharmaceutically acceptable aqueous injectable fluid. The carrier will be the largest component of the mixtures, commonly ranging from 60% to 99% by weight of the overall composition.

Preferred compositions have the following make ups:

| | |
|---|---|
| Collagen | 1 to 5% by weight |
| Crosslinker | 0.1 to 1% by weight |
| Flexible polymer | 0.5 to 5% by weight |
| Drug | 0.01 to 1% by weight |
| Carrier | 88 to 99% by weight to reach 100% of the overall injectable composition. |

Most commonly, the weight ratio of flexible polymer to collagen plus crosslinker is from about 0.02:1 to about 5:1. At the low end of this range, the flexible polymer is so minimal that its effect is negligible. At the high end, the flexible polymer begins to dominate the mixture. Preferred ratios are 0.1:1 to 1:1.

These compositions are portrayed in their simplest form. It will be readily appreciated that other components, ranging from preservatives to antibacterial agents to surfactants to tonicity adjusters or the like could be added if desired in the formulation of a finished product.

Depot Characteristics

Upon injection into a patient, the preferred injectable compositions of this invention undergo crosslinking in situ to form a matrix which acts as a drug release depot. In this role the depot restricts the release of drug and thus sustains its release over a longer period of time than would be realized if the matrix was not present.

In alternative embodiments, the drug can be released from a depot which is based on a preformed flexible polymer-containing crosslinked collagen matrix. This matrix can be formed from crosslinked collagen into which the drug and flexible polymer have been inserted prior to, during or after crosslinking. This matrix can be placed into an environment of use by injection in a suspension in a suitable injectable vehicle or, in the case of a solid body, could be implanted in the environment of use.

There are two characteristics of the matrix which define its diffusional resistance to solutes entrapped within it. One characteristic is the matrix's mesh or pore size (which is the spacing between bars in the cage created by the matrix polymer chairs); the other is the rigidity of the collagen chains making up the matrix (Johansson et al., *Macromolecules,* (1991) 24:6019.

Having a degree of rigidity is important because flexible polymer chains can distort and thus allow the drug to more readily diffuse out of the matrix. Thus in matrices with similar mesh sizes but different polymer chain rigidities, the primary resistance to diffusion in the more flexible matrix is thought to be frictional (Phillies, *J. Phys. Chem.,* (1989) 93:5029 in contrast to the more rigid matrix where the polymer chains act as immovable obstacles forcing the diffusing drug to take a tortuous path to leave the matrix (Doi et al., *The Theory of Polymer Dynamics,* Clarendon, Oxford (1986), chap. 9).

In collagen matrices, due to the rigidity of the collagen triple helix and also due to collagen's high length-to-diameter ratio, the molecules cannot be packed tightly enough to achieve desirable small pore sizes. Flexible polymers, on the other hand, because of their flexibility, are able to be packed more cohesively and thus attain smaller mesh sizes. Thus the intimate mixing of a flexible polymer within a collagen matrix effectively "chokes down" the matrix pore size by filling in spaces between collagen molecules, which collagen molecules themselves (because of their rigidity) cannot occupy.

The collagen matrix in turn has a reinforcing effect on the flexible polymer (by geometrically constraining it), which effectively makes the entwined flexible polymer more rigid. This interaction between rigid and flexible polymers has been illustrated in a model system. In this model system, a set of Electron Spin Resonance (ESR) experiments were carried out using spin-labeled polyacrylic acid in various mixtures with hyaluronic acid (a flexible polymer) and succinylated (but not crosslinked) collagen (a more rigid polymer). (V. Shenoy, *Controlled Release of Macromolecules from Biopolymer Matrices: Diffusional Effects,* M.S. Thesis, Univ. of Maryland, Baltimore (1993), chap 2). The mobility of the polyacrylic acid chain was severely impeded in concentrated collagen matrices relative to concentrated hyaluronic acid matrices.

This synergistic effect of the mixture of the flexible chain polymer with the crosslinked collagen matrix of the present invention, in reducing the effective pore size as well as in rigidifying the flexible chain gives more diffusional hindrance than a rigid polymer only or flexible polymer only matrix.

Another characteristic of the depots formed from the injectable compositions of this invention is that in order to achieve intimate mixing the rigid and flexible polymers should be like charged; otherwise they may tend to phase separate. Additionally, in the depot, the flexible polymer is preferably hydrophilic so that it will stretch out and entwine with the collagen.

The matrices of the present invention can have their pore sizes tailored to give desired rates of drug release. The largest possible pore sizes, which are achieved with the smallest proportions of flexible polymer, (and which are so large that they generally do not suitably restrict drug release), are 30 nm or so in the case of nonfibrillar-collagen-based matrices and up to 100 nm or 200 nm with fibrillar-collagen-based materials. Pore sizes can be tailored down to about 3 nm or even smaller, if desired, by increasing the collagen concentration or by increasing the proportion of flexible polymer. (See Rosenblatt et al., *Proc. Int. Symp. Control. Rel. Bioact. Mater,* (1993) 20:264.) Pore sizes for succinylated collagen matrices at 43 mg/ml are 3 nm and at 5 mg/ml are 30 nm. For hyaluronic acid matrices at a concentration of 30 and 8 mg/ml, the pore sizes are 3 nm and 30 nm, respectively. Fibrillar collagen matrices have much larger pore sizes (approximately 55 nm at 35 mg/ml. (See Rosenblatt et al., *J. Controlled Release* (1989) 9:195.) Another reference for hyaluronic acid mesh sizes that shows similar values to those above using probe methods is De Smedt et al., *Macromolecules* 22:141 (1994).

This matrix is stable. The crosslinking agents described above are capable of providing a matrix which will have a longer life than the desired sustained period of drug release. Typical lives for these matrices are from about 2 days to a year or more, depending upon the condition being treated and the course of therapy desired.

The matrix encloses the flexible chain polymer. This polymer entwines itself around the matrix elements and effectively "chokes down" the matrix pore size to a point that they become restrictive to the diffusion of drug out of the matrix. (This "new" pore size which results from the interaction of the flexible polymer with the collagen matrix is referred to as the "effective pore size". Effective pore sizes range from about 3 nM to about 100 nM and preferably range from about 10% to about 60%, and especially 10% to about 50% of the pore size which would be obtained if no flexible chain polymer were present.

As a general rule, the greater the proportion of flexible polymer present in the matrix, the greater the shrinking of the effective pore size until the obstructing effect of reduced poresize on diffusion rates is overcome by increasing the flexibility of the pores due to the proportion of flexible polymer present. Thus, one can adjust the release rate of a drug very simply by varying the relative proportions of collagen plus crosslinker and flexible chain polymer.

Preferably the matrix is crosslinked in situ so that erosion of the matrix is minimized and so the matrix can be implanted percutaneously. Since some modifications of collagen are thermally and/or hydrolytically unstable and sensitive to proteinases, crosslinking will stabilize the collagen and inhibit proteolytic dissolution. Also, since some non-crosslinked, modified collagens are soluble under physiologic conditions, a non-crosslinked, matrix can erode by solublization.

Methods of Preparation

The injectable compositions of this invention are typically prepared immediately prior to use. This preparation involves mixing the collagen, crosslinker, flexible chain polymer and drug in the injectable medium. The collagen and crosslinker will react typically within a few minutes or an hour, for example, 10 minutes to 2 hour. After crosslinking, the composition becomes a solid gel and cannot be easily injected.

The mixing can be carried out in any convenient manner. Intermixing between syringes or other equivalent manual operations prior to administration give good results.

The various components of the injectable compositions are described in the art together with their preparations. For brevity these preparations will not be repeated here.

Methods of Use

In use, the injectable compositions of this invention are injected into the body of the patient being treated. This injecting should be done in a manner which allows the injectable composition an opportunity to remain relatively nondispersed while the crosslinking takes place and the depot is formed. Accordingly, intravenous or intraarterial injection, which would lead to the rapid dispersal of the injectable composition are not preferred manners of delivery. Injection into less turbulent environments is preferred, for example subcutaneous, intradermal, intramuscular and intracranial injection are suitable. The amount of composition administered should be an amount which will provide an effective dose of the entrapped drug. The term "effective amount" refers to the amount of biologically active agent required in order to obtain the effect desired. The actual amount which is determined to be an effective amount will vary depending on factors such as the size, condition, sex and age of the patient and can be more readily determined by the caregiver.

Moreover, the rate of delivery desired may easily be determined by routine experimentation, for example by preparing a model composition following the examples below, and assaying the release rate in a suitable animal model.

EXAMPLES

The following examples are put forth so as to provide a complete disclosure and description of how to make the injectable compositions and the depots which they provide and are not intended to limit the scope of what the inventors regard as their invention. Efforts have been made to ensure accuracy with respect to numbers used (e.g., amounts, temperature, molecular weight, etc.) but some experimental errors and deviation should be accounted for. Unless indicated otherwise, parts are parts by weight, molecular weight is average molecular weight, temperature is in degrees Centigrade, and pressure is at or near atmospheric.

The present invention is shown and described herein at what is considered to be the most practical, and preferred embodiments. It is recognized, however, that departures may be made therefrom which are within the scope of the invention and that obvious modifications will occur to one skilled in the art upon reading this disclosure.

Example 1

(Preparation of Activated Crosslinker)

(C) Difunctional PEG 3400 (34 g, 10 mmol, Aldrich Chemical Co.) is dissolved in 1,2-dichoroethane (250 mL) and heated at reflux with glutaric anhydride (10 g) and pyridine (4 mL) under nitrogen for 3 days. The solution is then filtered and the solvent evaporated, and the residue dissolved in water (100 mL) and washed with diethyl ether (2×50 mL). The resulting PEG-diglutarate is extracted from the water with chloroform (2×50 mL), and the chloroform evaporated to yield PEG-diglutarate. The PEG-diglutarate is then dissolved in DMF (200 mL) at 37° C., and N-hydroxysuccinimide (10% molar xs) added. The solution is cooled to 0° C., and an equivalent amount of dicyclohexylcarbodiimide added in DMF solution (10 mL). The mixture is left at room temperature for 24 hours, and then filtered. Cold benzene (100 mL) is then added, and the PEG-di(succinimidyl glutarate) (dPEG-SG) precipitated by adding petroleum ether (200 mL) at 0° C. The precipitate is collected on a sintered glass filter. Dissolution in benzene, followed by precipitation with petroleum ether is repeated three times to provide "activated" dPEG (dPEG*).

Example 2

Gels were prepared by succinylating collagen according to the procedure of Miyata (U.S. Pat. No. 4,164,559 (1979)). The succinylated collagen (SC) was precipitated at pH 4.5 and concentrated by centrifugation. The pH was adjusted to 7.2 and the solution was buffered in 20 mM sodium phosphate and 130 mM sodium chloride by exhaustive dialysis against an aqueous solution of 20 mM sodium phosphate, 130 mM sodium chloride, adjusted to pH 7.2 (PBS). The concentration of the succinylated collagen was measured at this point at 45 mg/ml. For one matrix prepared in these experiments, the SC was diluted to 20 mg/ml with PBS prior to preparation of the matrix. A 20 mg/ml hyaluronic acid-drug solution was prepared by dissolving 100 mg of powdered hyaluronic acid and drug (powder) in 5 ml of PBS. For drugs in liquid form the liquid could be added to the hyaluronic acid (HA) solution and the volume of drug solution subtracted from the volume of PBS added. In principle there is no reason why the drug could not be added to the collagen solution. In these experiments 400 kDa fluorescein-labeled Ficol, hereafter referred to as "Ficol" (Molecular Probes, Inc., Eugene, Oreg.) was used as a model drug compound. A matrix with a final composition of 10 mg/ml SC, 10 mg/ml HA and 3 mg/ml Ficol was prepared by mixing 0.75 ml SC with 0.75 ml of HA solution. This 1.5 cc matrix was then mixed with 4.5 mg of powder Ficol. Mixing was accomplished by exchange between 3-cc syringes (100 passes). The mixture was allowed to equilibrate overnight. The mixture was crosslinked by mixing 10 mg of dry dPEG* powder with 1.5 cc of the HA-SC-Ficol solution. Mixing was performed between two 3-cc syringes (50 passes), one of which initially contained only dPEG* powder, the other containing the HA-SC-Ficol solution. The mixture was transferred into a 1-cc syringe and was allowed to cure overnight at room temperature (22° C.) during which it formed a firm cylindrical gel.

Another gel was prepared with a final composition of 16 mg/ml SC, 4 mg/ml HA and 3 mg/ml Ficol by mixing 0.96 ml of 25 mg/ml SC with 0.54 ml of 11.1 mg/ml HA. This 1.5 cc matrix was then mixed with 4.5 mg powder Ficol. A gel containing 30 mg/ml SC, 6 mg/ml HA and 3 mg/ml Ficol was prepared by mixing 1 cc of 45 mg/ml SC with 0.5 cc of 18 mg/ml HA. 1.5 cc of HA-SC mixture was mixed with 4.5 mg of dry powder Ficol. These gels were mixed and crosslinked using the identical procedure to the gel described above. Instead of allowing the gel to cure in the 1-cc syringe as was done here, the final mixture of materials could have been injected to form the drug delivery depot.

Example 3

Release of Fluorescein Labeled Ficol from 20 mg/ml Succinylated Collagen (SC) Hyaluronic Acid (HA) Matrices The Ficol-containing gels prepared in Example 2 were sectioned into cylinders measuring 22 mm in length×5.5 mm in diameter. All cylinders were trimmed to a mass of 500 mg. The cylinders were placed in 4-ml polypropylene vials and 2 ml of PBS was added such that a cylinder was completely submerged. The cylinders were allowed to sit at 22° C. for approximately 1 day. The PBS surrounding the cylinder was then removed and replaced with fresh PBS. The removed PBS was saved for measurement of the amount of Ficol released by fluorescence intensity measurement. The same elution procedure was repeated after another day to obtain a second time point. Release profiles for these gels were tested in duplicate. Gels consisting of Ficol (3 mg/ml) and SC (20 mg/ml) crosslinked with 7.5 mg/ml dPEG* were used as controls. Care was taken not to perturb the vials containing the gels during measurement.

At time points where eluting buffer was removed, the fluorescence intensity was read from 200 microliter samples in a model 7620 microplate fluorometer (Cambridge Technologies, Watertown, Mass.). Results are plotted in FIG. 1 as cumulative fluorescence released versus time for 20 mg/ml Succinylated collagen matrices, mixed 10 mg/ml SC-10 mg/ml HA matrices, and 16 mg/ml SC 4 mg/ml HA matrices. The values plotted represent the average of samples from two separate matrices and are expressed in Arbitrary Fluorescence Units or "A.F.U.s". The individual readings in all cases were within 5% of the average.

Results show that release was slower from the matrices containing 20% flexible polymer. For matrices containing 50% flexible polymer release was faster than for the rigid polymer only (SC only) matrix. It should be recognized that in these experiments the total weight of collagen plus crosslinker plus flexible polymer was held constant. Thus, at a 50/50 mixture, the amount of collagen providing rigidity to the matrix was substantially reduced.

Had the collagen content remained constant, the rate of drug release would have continued to drop even when an equal weight of flexible polymer was added.

Example 4

Release of Fluorescein Labeled Ficol from 36 mg/ml SC and HA Matrices

A release experiment similar to that in Example 4 was conducted for matrices comprised of 36 mg/ml SC and mixtures of 30 mg/ml SC and 6 mg/ml HA containing Ficol. Eluting buffer was refreshed at discrete time points and the number of fluorescent units from 200 microliter samples of eluting buffer were removed and read in a fluorometer. Cumulative fluorescent units released versus time are plotted in FIG. 2. The values plotted represent the average of samples from two separate matrices. The individual readings in all cases were within 5% of the average.

Figure 2:
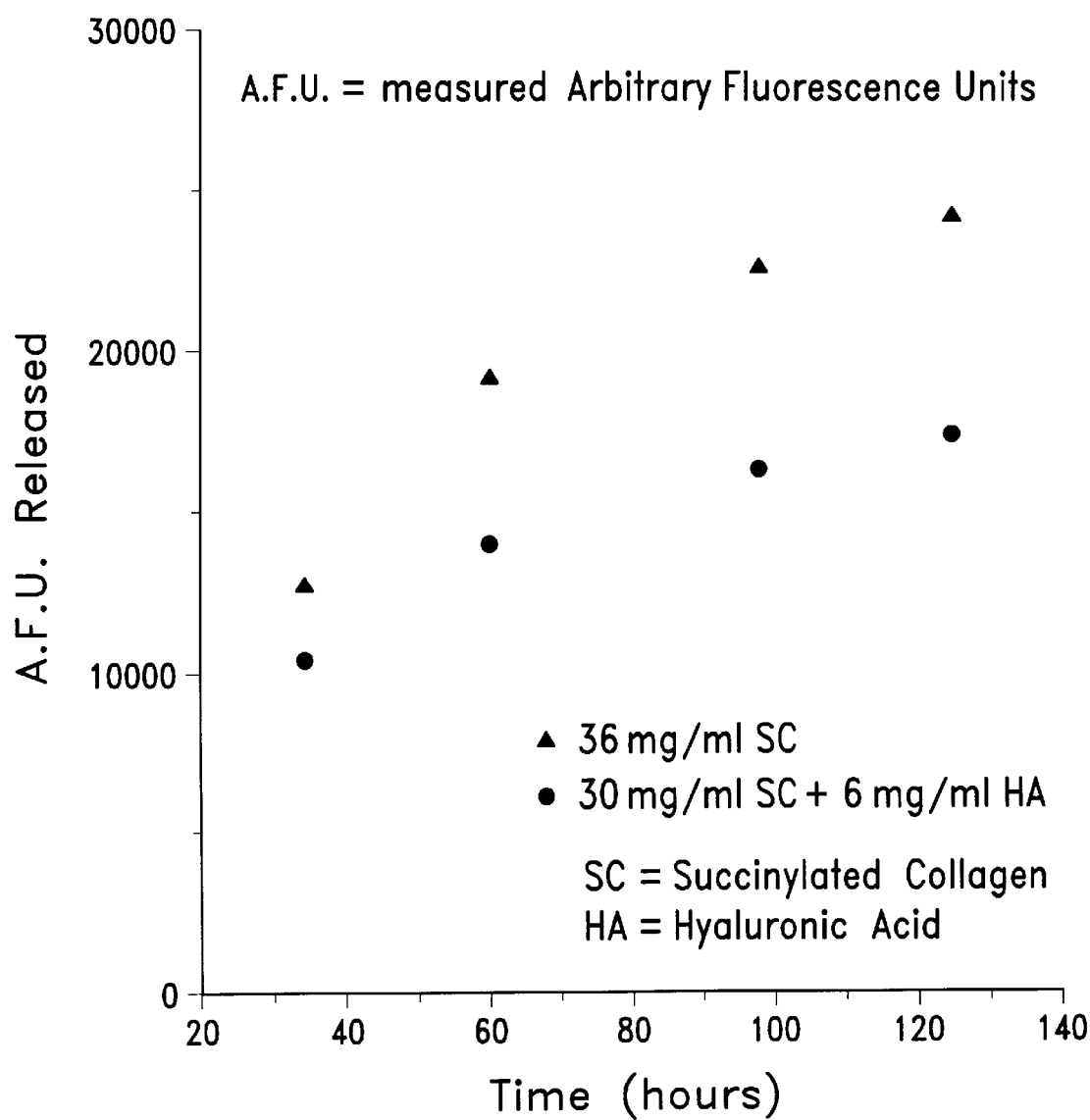
FIG. 2 is a graph illustrating the rate of drug release from a collagen matrix alone and the rate of release from a second matrix which additionally includes a flexible chain polymer.

The results of this experiment are provided in FIG. 2. They show that at higher rigid rod molecule concentrations the beneficial rate controlling effect of adding a flexible component to the matrix is more pronounced.

We claim:

1. An injectable pharmaceutically acceptable sustained-release drug delivery formulation comprising:
   i) collagen;
   ii) a crosslinking agent capable of forming covalent bonds with the collagen in situ following injection with the collagen;
   iii) a flexible chain polymer, wherein the flexible chain polymer is hydrophilic and has a molecular weight of at least about 100 kDa, a persistence length of less than about 10% of the persistence length of the collagen, and a charge similar in sign to that of the collagen;

iv) a drug; and v) a pharmaceutically acceptable injectable carrier;

wherein upon injection of the formulation into a patient, the crosslinking agent is capable of crosslinking the collagen in situ to form a porous matrix having both the drug and the flexible chain polymer entrapped therein, and wherein the crosslinked matrix is capable of sustained diffusion of the drug from the matrix.

2. The formulation of claim 1, wherein the collagen and the flexible chain polymer are each positively charged.

3. The formulation of claim 1, wherein the flexible chain polymer is a synthetic flexible chain polymer.

4. The formulation of claim 3, wherein the synthetic flexible chain polymer is selected from the group consisting of: poly(acrylic acid), poly(vinyl alcohol), poly(acrylamide), poly(N-isopropylacrylamide),poly(methacrylate), poly(hydroxyethylmethacrylate), poly(vinyl acetate), and copolymers thereof.

5. The formulation of claim 1, wherein the flexible chain polymer is a naturally occurring material.

6. The formulation of claim 5, wherein the naturally occurring flexible chain polymer is selected from the group consisting of glycosaminoglycans, celluloses, and poly(nucleic acid)s.

7. The formulation of claim 6, wherein the naturally occurring flexible chain polymer is a glycosaminoglycan.

8. The formulation of claim 7, wherein the naturally occurring flexible chain polymer is a glycosaminoglycan selected from the group consisting of: hyaluronic acid, chondroitin sulfate A, chondroitin sulfate B, chondroitin sulfate C, chitin, and chitosan.

9. The formulation of claim 1, wherein the collagen is fibrillar collagen.

10. The formulation of claim 1, wherein the collagen is atelopeptide collagen.

11. The formulation of claim 1, wherein the collagen is fibrillar atelopeptide collagen.

12. The formulation of claim 1, wherein the collagen is nonfibrillar atelopeptide collagen.

13. The formulation of claim 1, wherein the collagen has available at least one lysine residue for crosslinking.

14. The formulation of claim 9, wherein the fibrillar collagen is prepared by grinding or shredding collagenous tissue.

15. The formulation of claim 11, wherein the fibrillar atelopeptide collagen is prepared by dissolving tissue in aqueous acid followed by enzymatic digestion.

16. The formulation of claim 12, wherein the nonfibrillar atelopeptide collagen is prepared by dissolving tissue in aqueous acid followed by enzymatic digestion.

17. The formulation of claim 1, wherein the crosslinking agent is a synthetic hydrophilic polymer.

18. The formulation of claim 17, wherein the synthetic hydrophilic polymer is functionalized polyethylene glycol.

19. The formulation of claim 18, wherein the functionalized polyethylene glycol is difunctionalized.

20. The formulation of claim 19, wherein the difunctionalized polyethylene glycol is succinimidyl glutaryl polyethylene glycol.

21. The formulation of claim 1, wherein the drug has an apparent molecular weight of at least about 10 kDa.

22. The formulation of claim 1, wherein the drug is encapsulated in liposomes.

23. The formulation of claim 1, wherein the drug is a growth factor.

24. The formulation of claim 1, wherein the drug is a cytokine.

25. The formulation of claim 1, wherein the drug is Clotting Factor 9.

26. The formulation of claim 1, wherein the drug is PEGylated TGF-beta.

27. The formulation of claim 1, wherein the drug is erythropoietin.

28. The formulation of claim 1, wherein the drug is covalently attached to a carrier molecule.

29. The formulation of claim 28, wherein the carrier molecule is a glycosaminoglycan or a protein.

30. The formulation of claim 28, wherein the carrier molecule is starch.

31. The formulation of claim 28, wherein the carrier molecule is glycogen.

32. The formulation of claim 28, wherein the carrier molecule is fibrinogen.

33. The formulation of claim 28, wherein the carrier molecule is human albumin.

34. The formulation of claim 28, wherein the carrier molecule is monofunctional PEG.

35. The formulation of claim 28, wherein the carrier molecule is fibronectin.

36. The formulation of claim 28, wherein the carrier molecule is a lipid.

37. The formulation of claim 28, wherein the drug is an enzyme.

38. The formulation of claim 28, wherein the drug is a PEGylated protein.

39. The formulation of claim 28, wherein the drug is Clotting Factor 8.

40. A sustained-release drug delivery depot, for administration of a drug to an environment in a patient, comprising a drug and a flexible chain polymer wherein both the drug and the flexible chain polymer are entrapped within a porous matrix of collagen crosslinked with a crosslinking agent, wherein the pore size is less than 200 nanometers;

wherein the flexible chain polymer is hydrophilic and has a molecular weight of at least about 100 kDa, a persistence length of less than about 10% of the persistence length of the collagen, and a charge similar in sign to that of the collagen; and wherein the flexible chain polymer alters the effective pore size of a matrix of crosslinked collagen to a size capable of sustaining the diffusion of the drug from the matrix into surrounding tissues.

41. A method for preparing an injectable pharmaceutically acceptable composition capable of forming a sustained-release drug delivery depot in situ comprising the steps of.

i) providing:

a) a drug;

b) collagen;

c) at least one crosslinking agent capable of forming bonds with the collagen;

d) at least one flexible chain polymer, wherein the flexible chain polymer is hydrophilic and has a molecular weight of at least about 100 kDa, a persistence length of less than about 10% of the persistence length of the collagen, and a charge similar in sign to that of the collagen; and e) a pharmaceutically acceptable injectable medium; and ii) forming a pharmaceutically acceptable formulation comprising the components provided in (i);

wherein upon injection of the formulation into a patient, the crosslinking agent is capable of crosslinking the collagen in situ to form a porous matrix having both the drug and the flexible chain polymer entrapped therein, and wherein the crosslinked matrix is capable of sustained diffusion of the drug from the matrix.

42. The method of claim 41, wherein at least one crosslinking agent functions only to crosslink collagen.

43. A method for administering a drug to a patient comprising the steps of:
  i) forming a pharmaceutically acceptable formulation comprising:
    a) the drug;
    b) collagen;
    c) at least one crosslinking agent capable of forming covalent bonds with the collagen;
    d) at least one flexible chain polymer, wherein the flexible chain polymer is hydrophilic and has a molecular weight of at least about 100 kDa, a persistence length of less than about 10% of the persistence length of the collagen, and a charge similar in sign to that of the collagen; and
    e) a pharmaceutically acceptable injectable medium; and
  ii) injecting the pharmaceutically acceptable formulation into the patient under conditions which limit the immediate dispersion of the formulation, and permitting the crosslinking agent to crosslink the collagen in situ to form a porous matrix comprising the drug and capable of sustained release of the drug, wherein the pores of the matrix are limited in size by the presence of the flexible chain polymer, and wherein the drug is able to diffuse through the pores to the patient.

44. The formulation of claim 1 wherein the formulation includes about 1 to 5% collagen by weight, about 0.1 to 1 % crosslinker by weight, and about 0.5 to 5% flexible polymer by weight.

45. The formulation of claim 1 wherein the weight ratio of flexible polymer to collagen plus crosslinker is between about 0.02:1 to about 5:1.

46. The formulation of claim 1 wherein the weight ratio of flexible polymer to collagen plus crosslinker is between about 0.1:1 to 1:1.

47. The method of claim 43 wherein size of the pores is less than 200 nanometers.

48. The method of claim 43 wherein the crosslinking agent comprises a synthetic hydrophilic polymer.

49. The drug delivery depot of claim 40 wherein the crosslinking agent comprises a synthetic hydrophilic polymer.

* * * * *